United States Patent [19]

Sauerwein et al.

[11] Patent Number: 5,047,851
[45] Date of Patent: Sep. 10, 1991

[54] PROCESS AND DEVICE FOR DETECTING AND EVALUATING SURFACE CRACKS IN WORKPIECES

[75] Inventors: Kurt Sauerwein, Erkrath; Hans P. Busse, Wuppertal; Rainer Link, Kerpen-Horrem; Helmut Wiacker, Hilden; Christian Stapf; Rüdiger Schulz, both of Wuppertal; Ekhard Stolzenberg, Wülfrath; Kurt Disselhorst, Solingen; Herbert Burghoff, Wermelskirchen; Karl Kirchesch, Düsseldorf, all of Fed. Rep. of Germany; James D. Lean, London; Laurence F. Topping, Romford, both of Great Britain; Wolfgang Zindler, Dormagen, Fed. Rep. of Germany

[73] Assignees: Isotopen-Technik Dr. Sauerwein GmbH; Ford Werke AG, both of Köln-Niehl, Fed. Rep. of Germany

[21] Appl. No.: 485,133

[22] Filed: Feb. 26, 1990

Related U.S. Application Data

[63] Continuation-in-part of Ser. No. 249,356, Sep. 23, 1988, abandoned.

[30] Foreign Application Priority Data

Sep. 23, 1987 [DE] Fed. Rep. of Germany ....... 3731947

[51] Int. Cl.$^5$ .............................................. H04N 7/18
[52] U.S. Cl. .................................. 358/101; 358/106; 382/8
[58] Field of Search ....................... 358/101, 106, 107; 382/8

[56] References Cited

U.S. PATENT DOCUMENTS

| | | | |
|---|---|---|---|
| 4,484,081 | 11/1984 | Cornyn, Jr. et al. | 358/106 X |
| 4,716,459 | 12/1987 | Makabe et al. | 358/106 |
| 4,735,323 | 4/1988 | Okada et al. | 358/106 X |
| 4,741,042 | 4/1988 | Throop et al. | 382/8 X |

Primary Examiner—Victor R. Kostak
Attorney, Agent, or Firm—Toren, McGeady & Associates

[57] ABSTRACT

A process and device for detecting and evaluating surface cracks in workpieces wherein a picture is produced of the surface of the workpiece by means of a video camera and said picture is digitized and is processed by means of a computer to produce a binary picture of any cracks present and a sorting report is triggered when a preselected threshold level is exceeded. In order to obtain a sorting signal that is independent of the absolute brightness of the original picture a blurred background picture is derived from the original picture levels that have been converted to digitized grey shade levels and subtracted from the original picture, the difference picture formed in this way giving the crack representation. A dynamic threshold level for the sorting signal is determined by comparing the grey shade distribution of the original or the difference picture with at least one previously evaluated or difference picture and a binary picture is produced from the original or the difference picture and the grey shade threshold, and picture elements with their gray shades exceeding the set threshold are indicated as defects. The surface of the workpiece may be pre-treated by the magnetic powder or dye penetration process and/or contrast intensifying means.

9 Claims, 1 Drawing Sheet

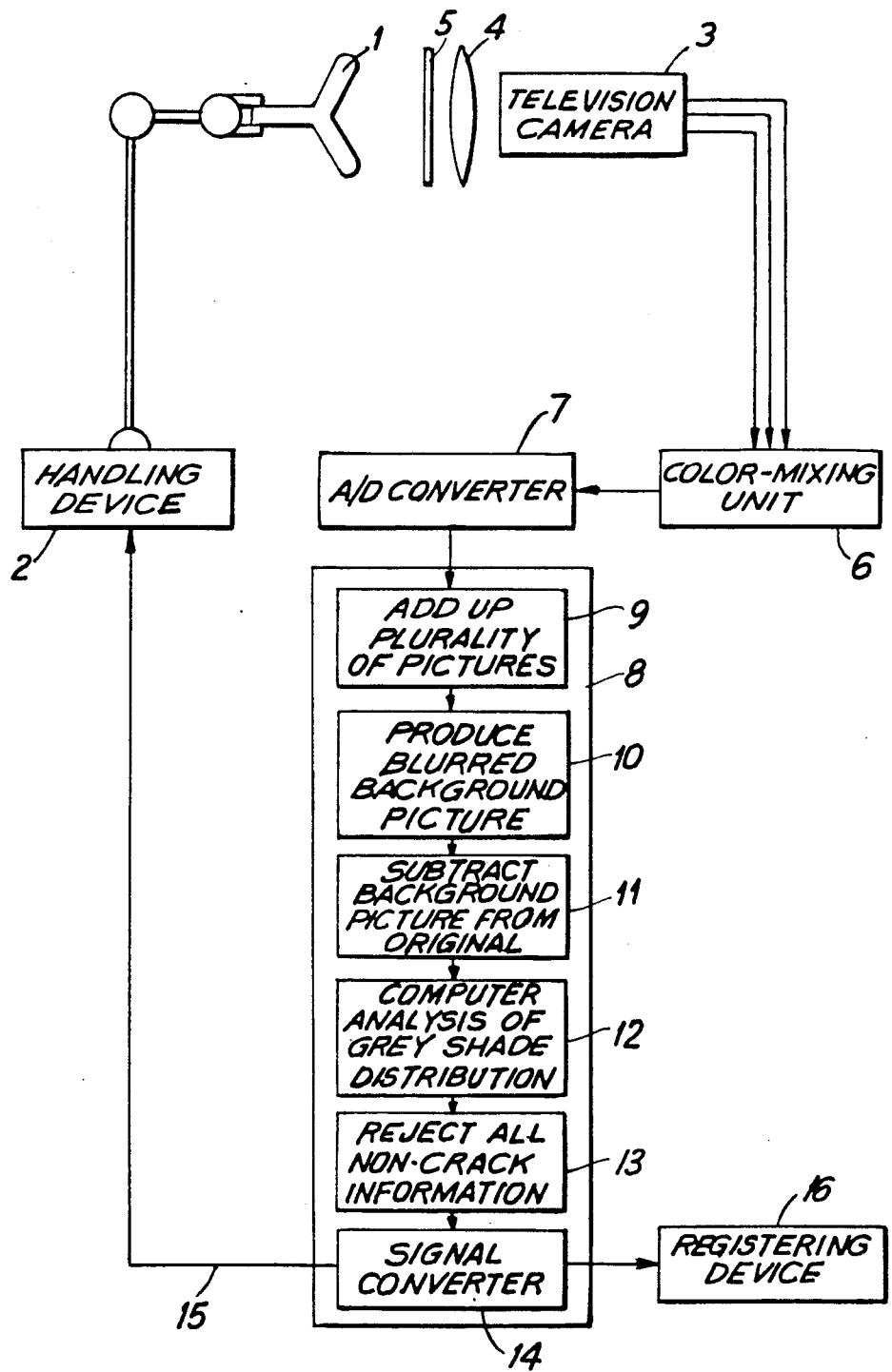

PROCESS AND DEVICE FOR DETECTING AND EVALUATING SURFACE CRACKS IN WORKPIECES

This is a continuation-in-part application of Ser. No. 07/249,356, filed Sept. 23, 1988, now abandoned.

TECHNICAL FIELD OF THE INVENTION

The invention relates to a process and a device for detecting and evaluating surface cracks in workpieces, wherein a picture is taken of the surface of the workpiece by means of a video camera and said picture is digitized and is processed by means of a computer so as to produce a binary picture of any cracks present, and a sorting report is triggered when a preselected threshold level is exceeded.

BACKGROUND OF THE INVENTION AND PRIOR ART

A process of this kind and a corresponding device are known from DE-OS 34 40 437.

Crack detecting processes are required in particular in the mass production of components that are particularly important from the point of view of safety, as surface cracks form a considerable danger. This is particularly the case for motor vehicle components which are manufactured in large quantities but have to be examined individually for the presence of cracks. The visual evaluation of defect indications by an inspector is a considerable strain since the probability of defects occurring is very small and this affects the inspector's ability to concentrate. As a result, the probability of defect detection suffers.

In the known process the inspection is carried out automatically by digitising the picture information of the camera picture of the grey shades and storing the digital values obtained in this way as a matrix of picture elements (pixels) in a semiconductor store. By means of a computer, in a first processing step, a binary picture is produced from this and in a second processing step all indications of linear and punctiform structures are eliminated whose extent does not exceed a preselected number of picture elements. In a third processing step the remaining indications of surface structures are enlarged in each image direction to a size exceeding their original extent by at least one picture element; the binary picture obtained in this way is extracted from the output binary picture as a mask covering all surface structures. Finally, the remaining binary picture is scanned in rows or columns for evaluation. The picture elements comprising indications that are detected by this means are counted, and a sorting report is triggered if, when a series of picture elements directly adjoining one another is scanned, a preselected minimum number of indications have been counted.

Since in the known process a binary picture is produced in the first step there is no simple way of improving the signal-to-noise ratio. In addition, the binary picture produced according to the known process is not independent of the absolute brightness of the original picture, nor can changes in the installation be indicated, for example a decrease in the intensity of illumination, a change in the composition of the crack representing agent or the effect of dust. The use of a black and white television camera also greatly restricts the possibility of analog signal preprocessing.

OBJECT OF THE INVENTION

It is therefore the object of the invention to provide a process and a device which gives a way, suitable for use in industrial mass production, of achieving very high resolution in the automatic detection and evaluation of cracks while eliminating environmental influences and background interference.

BRIEF DESCRIPTION OF THE INVENTION

To this end, according to the invention, in a process of the kind described in the introduction a blurred background picture is derived from the original picture levels converted to digitized grey shade levels and subtracted from the original picture, or the original picture is subjected to suitable high-pass filtering and the difference picture or high-pass filtered picture formed in this way gives the crack representation. The background picture is produced by a low-pass filter or by some other mathematical operation. The subtraction from the original picture results in a difference picture that does not show any structures which change slowly in the local area, but only parts having high local frequencies, for example those having crack-like structures. To avoid false indications a check is made of whether a crack really is involved by making an area, length or breadth test, for example by checking for a preselected length-to-breadth ratio.

In further embodiment of the process a dynamic grey shade threshold is determined by comparing the grey shade distribution of the original or the difference picture with at least one previously evaluated original or difference picture, producing a binary picture from the original or the difference picture and the grey shade threshold and indicating picture elements having grey shades exceeding the set threshold as defects. In this manner the automatic evaluation system working according to the process of the invention can be used in a production plant, since alterations in the plant, for example a reduction in the intensity of illumination, a change in the composition of the crack representing agent or dust effects can be recognised by the comparison with previously evaluated parts.

By subtracting the blurred background picture from the original picture a difference picture is produced which is independent of the absolute brightness of the original picture.

The surface of the workpiece may be pre-treated by the magnetic powder or dye penetration method and/or contrast intensifying agents.

The defect indication obtained through the binary picture is advantageously passed to the workpiece handling system and controls it so as to separate out the workpiece concerned.

In order to improve the signal-to-noise ratio in the digitized grey shade levels some of the television pictures picked up by the camera can be added up in television real time. With a picture frequency of 25 pictures per second and an integration time of 1 to 2 seconds this gives 25 to 50 integrated pictures of which the grey shade levels have a considerably reduced background noise.

It is particularly advantageous to perform the picture pick-up by means of a colour television camera in which the background picture is masked out by means of a filter adapted to the light emanating from the crack representation agent. This can be achieved if the optical filter substantially only allows the fluorescent light produced by the crack representation agent when the workpieces are illuminated to pass through to the pick-up part of the camera.

If a colour-mixing unit is also connected after the colour television camera, analog signal preprocessing can be performed by mixing the colours red, green and blue. This mixing is done in such proportions that the picture to be evaluated is separated from a background or spurious signal and other signals are filtered and/or amplified.

A device for carrying out the process according to the invention is characterised by a workpiece handling device, a colour television camera provided with an optical filter adapted to the light emanating from the crack representation agent, a colour-mixing unit connected thereafter, an analog-digital signal converter and a digital picture processing unit having a picture store and a computer unit to prepare and analyse the digital picture shades and having a control output connected to the workpiece handling machine.

BRIEF DESCRIPTION OF THE DRAWINGS

The invention will now be described in more detail with reference to an exemplary embodiment shown diagrammatically in the drawing.

DETAILED DESCRIPTION OF A PREFERRED EMBODIMENT OF THE INVENTION

A workpiece 1 which can be moved by a handling device 2 is located, in order to detect cracks, in front of a colour television camera 3 having a lens 4 and an optical filter 5 arranged in front of it. The workpiece 1 is treated by the magnetic particle or dye penetration process, possibly with the use of contrast intensifying means, and is illuminated by means of a light source (not shown) so that any cracks proceeding from the surface can be detected through the fluorescent light emanating from these cracks.

By means of the optical filter 5 the background picture can be largely masked out, so that essentially only fluorescent light reaches the pick-up part of the colour television camera 3 through the lens 4. The colour television camera produces signals for the colours red, green and blue which are fed to a colour-mixing unit 6. With the aid of this electronic colour-mixing unit 6 the colours can be mixed with one another in any desired proportions so as to filter out any further background and spurious signals or to highlight particular regions of the picture. Analog signal preprocessing thus takes place in the colour-mixing unit 6.

By way of an analog-digital signal converter 7 the picture reaches a digital picture processing unit 8 where, converted to grey shade levels, it is recorded in a picture store. In order to improve the signal-noise ratio a plurality of television pictures are added up in television real time. With a picture frequency of 25 pictures per second and an integration time of 1 to 2 second this gives 25 to 50 integrated pictures. This step of improving the signal-to-noise ratio is indicated in the drawing by the reference numeral 9. The next step, indicated by the reference numeral 10, consists in producing a blurred background picture from the original grey shade picture by passing this through a low-pass filter or subjecting it to some other mathematical operation.

In the next step 11 the blurred background picture is subtracted from the original picture so as to obtain a difference picture that does not include any structures changing slowly in the local area, but only parts with high local frequencies, for example crack-like structures. Step 12 consists in a computer analysis of the grey shade distribution in the original picture and in the difference picture and in a comparison of these levels with those of at least one previously evaluated workpiece. By this analysis alterations in the whole installation comprising the camera, lamps, crack representation agent etc. can be detected and a dynamic grey shade threshold can be set to test for defect signals. With the aid of this dynamically set grey shade threshold a binary picture in which all grey shades of the grey shade picture which exceed the set threshold appear light and vice versa is obtained from the grey shade picture.

In step 13 the binary picture is analysed by rejecting all binary information which does not relate to crack-like structures, while those remaining picture elements above the set threshold are indicated as defects and are processed in a signal converter 14 and passed as control signals via a control line 15 to the handling device 2 and to an indicating and registering device 16.

Alternatively a high-pass filtering operation can be performed on the original picture in order to obtain the crack representation. The relatively indistinct picture picked up by the television camera is again first of all integrated over several television pictures, i.e. the pictures are summed and standardised to 256 grey shades. This picture is high-pass filtered using a filter matrix. This corresponds to a low-pass filtering (production of a background picture) and difference to the original picture. The high-pass filter matrix used consists of $7 \times 7$ matrix elements that are adapted to the test problem.

In the high-pass picture mean values of the grey shade distribution and standard deviation of the noise part are formed. The grey shade picture is, as already described, converted by the threshold level operation to a binary picture.

The coordinates of the remaining binary points are determined. Crack indications that are interrupted by less than, for example, 4 pixels (picture elements) are first of all supplemented and completed. The length-to-breadth ratio is then determined. If this is greater than, for example, 2, it is identified as a crack indication, provided that the total number of the pixels is greater than, e.g., 20. The numerical levels given must be adapted to the test problem, so that for a particular article crack detection can be reliably performed with the least possible computer effort.

With the process and the device according to the invention it is possible to detect surface cracks in workpieces in a simple manner and to sort the workpieces. The process is highly sensitive and is largely unaffected by environmental influences as well as being independent of the geometry of the workpiece. At the same time changes in the installation can be detected and discounted.

What is claimed is:

1. A device for detecting and evaluating surface cracks in workpieces, comprising:
    workpiece handling means for holding a workpiece;
    a color television camera provided so as to view the workpiece held in the handling means, the camera having an optical filter adapted to light emanating from a crack representation agent, the camera producing a picture output including the colors red, green and blue;

a color-mixing unit connected to the camera output for mixing the colors and producing a corresponding output;

an analog-digital signal converter provided as to convert the output of the color-mixing unit;

a digital picture processing unit having a picture store, the processing unit being provided so as to receive the converted output; and a computer unit arranged so as to prepare and evaluate digital picture levels and having a control output connected to the workpiece handling device.

2. A process for detecting and evaluating surface cracks in work pieces, comprising the steps of taking a picture of the surface of a workpiece with a color video camera; masking out the background picture with a filter adapted to light emanating from a crack representation agent; performing analog signal processing by means of a color mixing unit by mixing the colors red, green and blue in such proportions that the picture to be evaluated is a background and/or spurious signal and other signals are filtered and/or intensified; digitized the picture; processing the picture with a computer to produce a binary picture of any cracks present; deriving a blurred background picture from the picture shades converted to digitized grey shade levels; subtracting the blurred background picture from the original picture to provide a different picture which gives the crack representation; and triggering a sorting report when a preselected threshold level is exceeded.

3. A process according to claim 1, including subjecting the original picture to high-pass filtering so that the high-pass filtered picture gives the crack representation.

4. A process according to claim 2, including setting a dynamic shade threshold by comparing the grey shade distribution of one of the original and the difference picture with at least one previously evaluated picture or a difference picture, producing a binary picture from the original or the difference picture and indicating the grey shade threshold and picture elements with their grey shades above the set threshold as defects.

5. A process according to claim 4, and further including controlling a workpiece handling system when a defect is indicated to separate the workpiece concerned.

6. A process according to claim 2, including adding up a plurality of pictures converted to grey shade levels.

7. A process according to claim 2, wherein including examining at least one of the length-to-breadth ratio and the area of the picture elements of the binary picture as criterion of a crack indication.

8. A process according to claim 2, including pretreating the workpiece by at least one of a magnetic powder or dye penetration method and contrast intensifying agents.

9. A process according to claim 3, including pretreating the workpiece by at least one of a magnetic powder or dye penetration method and contrast intensifying agents.

* * * * *